United States Patent
Stamper et al.

(10) Patent No.: US 6,179,876 B1
(45) Date of Patent: Jan. 30, 2001

(54) ORTHOPEDIC PROSTHESIS WITH CEMENT COMPRESSION RING AND METHOD

(76) Inventors: Blake A. Stamper, 2000 Hwy. 95, Suite 200, Bullhead City, AZ (US) 86442; Charles D. Guthrie, 1039 Kingsview Ct., Henderson, NV (US) 89015

( * ) Notice: Under 35 U.S.C. 154(b), the term of this patent shall be extended for 0 days.

(21) Appl. No.: 09/432,901

(22) Filed: Nov. 2, 1999

Related U.S. Application Data

(60) Provisional application No. 60/107,040, filed on Nov. 4, 1998.

(51) Int. Cl.$^7$ ..................................................... A61F 2/30
(52) U.S. Cl. ................................. 623/18.11; 623/16.11; 623/20.32
(58) Field of Search ........................... 623/16.11, 18.11, 623/20.14, 20.15, 20.32, 23.48; 606/92, 93, 94, 86, 88

(56) References Cited

U.S. PATENT DOCUMENTS

| | | | |
|---|---|---|---|
| 4,285,071 | 8/1981 | Nelson et al. | 3/1.912 |
| 4,593,685 | 6/1986 | McKay et al. | 128/92 |
| 5,171,276 | 12/1992 | Caspari et al. | 623/16 |
| 5,201,768 | 4/1993 | Caspari et al. | 623/20 |
| 5,326,363 * | 7/1994 | Aikins | 623/18.11 |
| 5,876,460 | 3/1999 | Bloebaum | 623/18 |
| 6,045,581 * | 4/2000 | Burkinshaw | 623/18.11 |

FOREIGN PATENT DOCUMENTS 0 650 707 A1   10/1994   (EP) .

* cited by examiner

*Primary Examiner*—Pedro Philogene
(74) *Attorney, Agent, or Firm*—Philip S. Lyren; Kenneth S. Barrow

(57) ABSTRACT

A compression ring for use in implanting an orthopedics prosthesis, the ring having an interior surface generally conforming to a peripheral wall of a base plate of the prosthesis, the compression ring being adapted to extend beyond a lower surface of the prosthesis, forming a cavity bounded by the lower surface and the compression ring. Also, a kit consisting of an orthopedic appliance having a base plate with a peripheral wall and a lower surface adapted to abut a resected bone surface, and a compression ring having an interior surface generally conforming to the peripheral wall of the base plate and slidingly received thereon, the compression ring being adapted to extend beyond the lower surface, forming a cavity bounded by the lower surface and the compression ring. Also, a method of implanting an orthopedic component using a compression ring on the component, by forming a cavity bounded by a surface of the orthopedic component and the compression ring, filling the cavity with bone cement, and securing the orthopedic component over a resected bone surface with the cavity between the component and the resected surface.

30 Claims, 2 Drawing Sheets

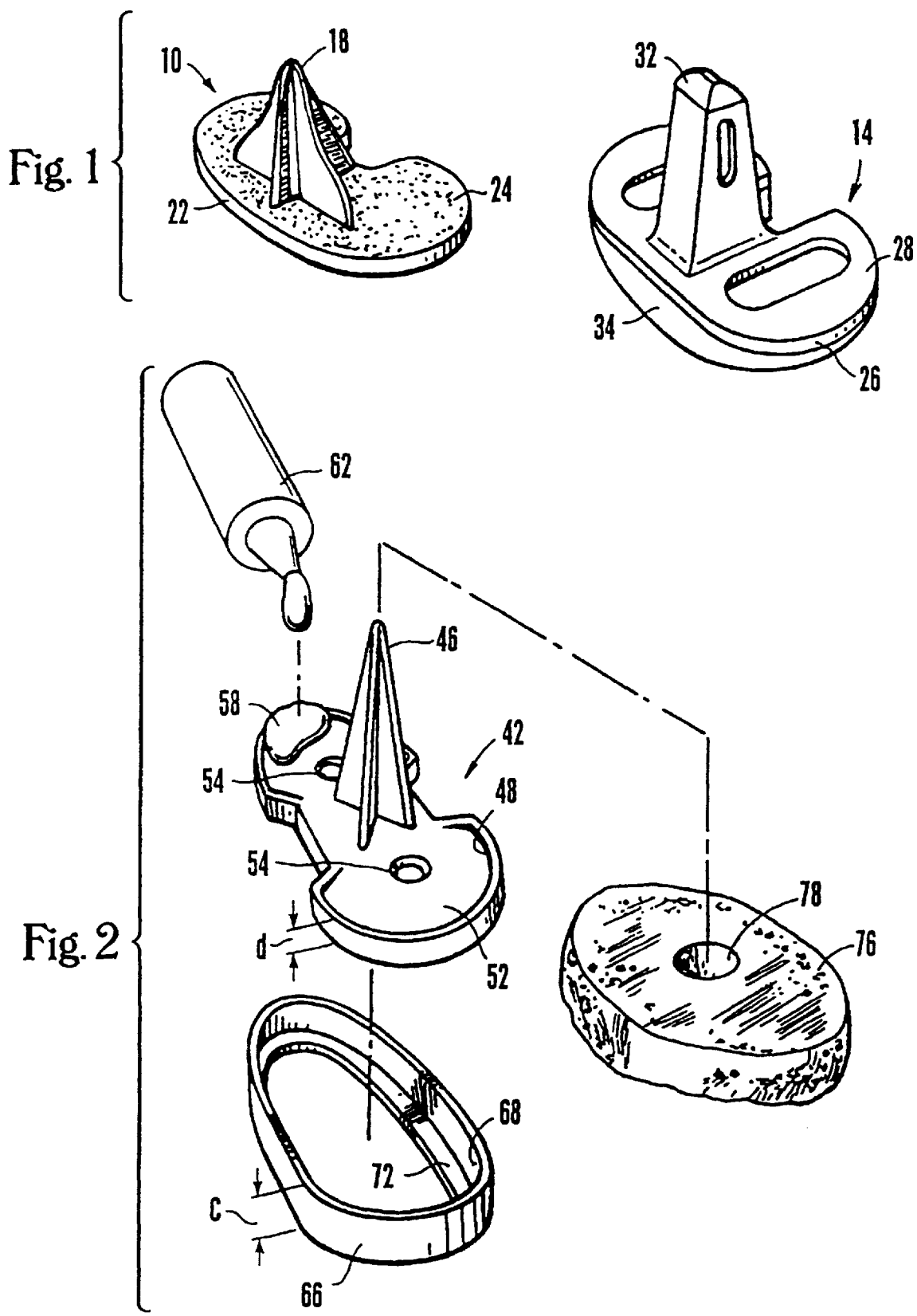

ORTHOPEDIC PROSTHESIS WITH CEMENT COMPRESSION RING AND METHOD

This application claims priority from U.S. provisional application 60/107,040, filed Nov. 4, 1998, incorporated herein by reference.

BACKGROUND OF THE INVENTION

1. Field of the Invention

This invention relates to implantable prostheses for joints such as knee, shoulder or other joints.

2. Background of the Invention

All joints of the body, including the knee, are vulnerable to injury and to damage by diseases. When joints are too diseased or injured for a microsurgical remedy, a prosthetic device may replace the joints. Since the 1970s, knee replacement surgery has offered persons with debilitating knee pain a chance to resume an active lifestyle. Also known as total knee arthroplasty, the procedure has become as successful as hip replacement surgery, which is considered to be one of this century's best-known medical advances.

The knee joint permits a wide range of motion that includes not only bending, but also sliding, gliding, and swiveling motions. This joint is also constructed to absorb the large forces generated during walking, running, and jumping maneuvers. Much like a hinge, the bottom end of the femur rests on top of the tibia, and when the knee bends, the ends of these two bones move against one another. Ligaments connect the femur to the tibia, while muscles and tendons stabilize the joint and enable it to move. The patella (knee cap) helps protect the joint and anchors important tendons.

Knee replacement surgery involves removing or resurfacing parts of the femur, tibia, and/or patella, and putting in a prosthesis made of metal alloy and high-density plastic. The most common reason for knee-replacement surgery is osteoarthritis, which causes a gradual deterioration of the cartilage between the tibia and femur, resulting in pain as the bones begin to rub together. Other reasons for knee surgery include rheumatoid arthritis (an autoimmune inflammation of the tissue surrounding the joints) and post-traumatic arthritis, which can occur years after an injury to the knee.

The prosthesis used in total knee arthroplasty will typically consist of several disconnected parts. One of the largest is fabricated out of a metal alloy, and attaches to the end of the femur after all diseased bone has been removed. Another major component, also fabricated of a metal alloy, resembles a tray on a pedestal. The pedestal is anchored into the tibia, and the platform has a surface of high-density plastic that acts as a bearing surface for the femur. If the patella has also been damaged, the knee replacement prosthesis may include a small circular piece of plastic that is attached to the patella, replacing cartilage and/or diseased bone.

In addition to the anchoring provided by having the metal prosthesis components physically inserted into bone tissue, two other techniques are available to insure a secure, durable connection between bone and prosthesis. A cementless prosthesis has a roughened, porous surface that is intended to enhance the ability of the bone tissue to grow directly into and around the metal component.

Cementless prosthesis unfortunately have shown a greater tendency for early loosening as well as for developing other long-term problems. The majority of orthopedic surgeons prefer to make use of bone cement to enhance the connection between the metal prosthesis members and the surrounding bone tissue. Methyl methacrylate is the most commonly used bone cement material.

In recent years there have been many improvements in techniques used for total knee arthroplasty. Nevertheless, tibial component loosening remains one or the most frequent modes of failure. Studies have indicated that bone cement pressurization and penetration are factors for increasing the strength of the bone-prosthesis interface. Present methods provide for relatively good cement penetration in the central areas of the bone-prosthesis interface. Unfortunately, leakage of cement around the periphery of the metal component during insertion results in relatively poor cement penetration around the outer edges of the prosthesis. Studies have suggested that a uniform cement penetration of 3–5 mm over the entire bone surface is desirable when attaching the prosthesis member to the underlying bone tissue.

It is an object of our invention to provide an apparatus for use with an orthopedic prosthesis for controlling and compressing cement during implantation of the prosthesis to provide uniform cement penetration.

It is also an object of our invention to provide a kit comprising an orthopedic prosthesis and a ring adapted to engage the prosthesis while cement is used to secure the prosthesis to bone such that a more secure and uniform cement mantel is formed.

It is further an object of our invention to provide a method for installing an orthopedic prosthesis whereby a more uniform cement penetration can be obtained.

SUMMARY OF THE INVENTION

Our invention comprises a compression ring for use in implanting an orthopedics prosthesis, the ring having an interior surface generally conforming to a peripheral wall of a base plate of the prosthesis, the compression ring being adapted to extend beyond a lower surface of the prosthesis, forming a cavity bounded by the lower surface and the compression ring.

Our invention also comprises a kit consisting of an orthopedic appliance having a base plate with a peripheral wall and a lower surface adapted to abut a resected bone surface, and a compression ring having an interior surface generally conforming to the peripheral wall of the base plate and slidingly received thereon, the compression ring being adapted to extend beyond the lower surface, forming a cavity bounded by the lower surface and the compression ring.

Further, we have invented a method of implanting an orthopedic component comprising the steps of providing an orthopedic appliance having a base plate, said base plate having a first surface adapted to abut a resected bone surface, and a peripheral wall, installing a compression ring on the appliance, the compression ring having an interior surface generally conforming to the peripheral wall and slidingly received thereon, extending said compression ring beyond said first surface, thereby forming a cavity bounded by the first surface and the compression ring, filling the cavity with bone cement, placing said orthopedic appliance over a resected bone surface with the cavity between the appliance and the surface, and removing the compression ring.

BRIEF DESCRIPTION OF THE DRAWINGS

FIG. 1 is a perspective view showing a pair of tibial baseplates of alternative design for use in accordance with the present invention;

FIG. 2 is an exploded, partial perspective view showing the manner in which a tibial component is received by a tibia in accordance with the present invention;

DETAILED DESCRIPTION OF PREFERRED EMBODIMENTS

Figure 3:
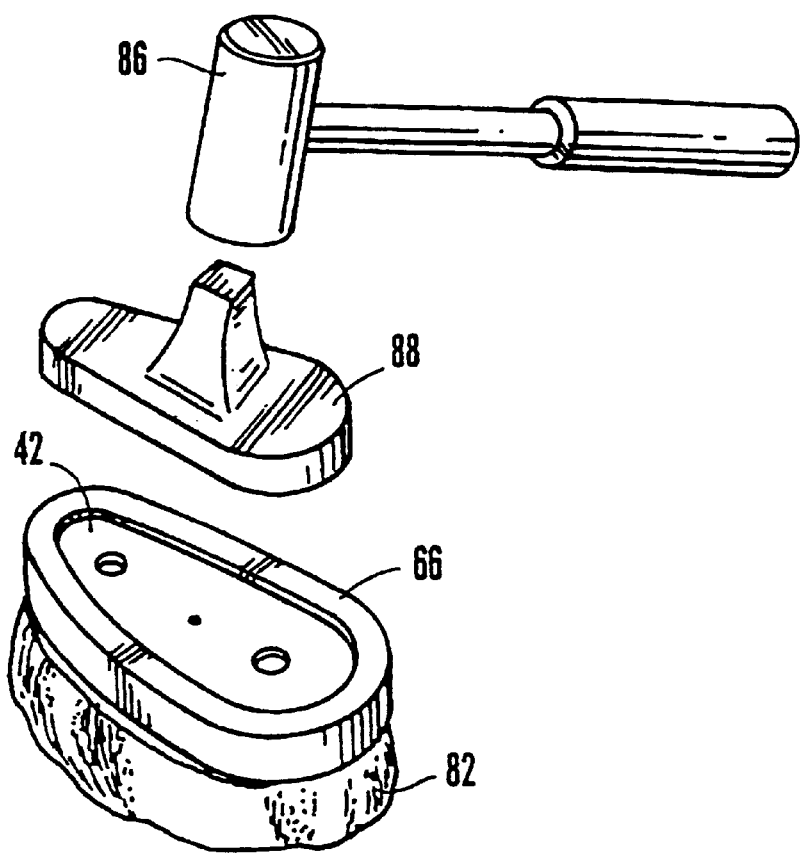
FIG. 3 is a partial perspective view showing a tibial component being secured to a tibia in accordance with the present invention.

Reference is now made to the drawings wherein like numerals refer to like parts throughout. In FIG. 1, a pair of tibial baseplates are shown, including a stemmed porous tibial baseplate 10 and a stemmed non-porous tibial baseplate 14. A central cruciate stem 18 projects from a first tibial tray 22 of the porous tibial baseplate 10. A continuous porous coating 24 is formed on the inferior surface of the first tibial tray 22. Baseplates having a porous coating are not used in the practice of the present invention.

The non-porous tibial baseplate 14 utilizes a second tibial tray 26 having a smooth inferior surface 28. A square stem 32 projects from the second tibial tray 26, and a polyethylene insert 34 is attached to the opposite, superior side of the second tibial tray 26. As noted previously, the polyethylene insert 34 replaces the diseased or damaged cartilage in the replacement joint.

An asymmetric tibial baseplate 42 is shown in FIG. 2, with the asymmetry provided to optimize tibial plateau coverage. A central cruciate stem 46 projects from the smooth inferior surface 28 in a manner similar to that shown by the porous tibial baseplate 10 of FIG. 1. Tibial stems provide additional stability to the baseplate mounting. Where required, utilizing even longer stems can provide enhanced stability.

As is shown in FIG. 2, a peripheral rim 48 is formed about an asymmetric, smooth inferior surface 52 of the asymmetric tibial baseplate 42. A pair of cancellous bone screw holes 54 are formed in the asymmetric, smooth inferior surface 52 at locations intended to provide fixation in the area of greatest cancellous bone density when the asymmetric tibial baseplate 42 is attached to its appropriate location on a tibia.

The asymmetric smooth inferior surface 52 provides a receiving surface for a layer of bone cement 58 shown being applied from a bone cement applicator 62. When methylmethacrylate is used as the bone cement, its "set time" is generally 12–15 minutes. In order to obtain an appropriate bone-cement penetration level, the tibial baseplate 42 is ordinarily installed within bone tissue within a 3–4 minute time frame (depending upon room temperature, adhesive viscosity, and other operating room parameters) after the bone cement 58 has been applied to the receiving surface.

A cement compression ring 66 provides a circumferentially-extended peripheral wall 68, with an attached seating ring 72. In accordance with the present invention, the cement compression ring 66 generally conforms to the outer periphery of the tibial baseplate. The peripheral wall 68 extends beyond the inferior surface 52 of the tibial baseplate 42, thereby enhancing the retention of bone cement within the prosthesis-bone tissue interface during securement of the prosthesis. This multi-piece apparatus is now ready for installation into bone tissue, which is depicted in FIG. 2 as a prepared tibial surface 76 having a central intermedullary canal 78.

It should be understood that although each of the tibial baseplates depicted in the drawing are provided with a stem, not all tibial baseplates have such stems. Moreover, such stems are not considered to be necessary for the practice of the present invention.

In FIG. 3, the tibial baseplate 42 and the cement compression ring 66, have been placed upon a prepared end of a tibia 82. The tibial baseplate 42 is preferably pressed onto the tibia 82 using a mallet 86 and a tibial baseplate impactor 88. The extended peripheral wall 68 contacts the prepared tibial surface first, then the tibial baseplate 42 is advanced, sliding within the cement compression ring 66. The peripheral wall 68 limits leakage about the periphery of the tibial baseplate interface, thereby increasing pressure within the cement column and improving penetration of cement into the cancellous bone surface.

Figure 4:
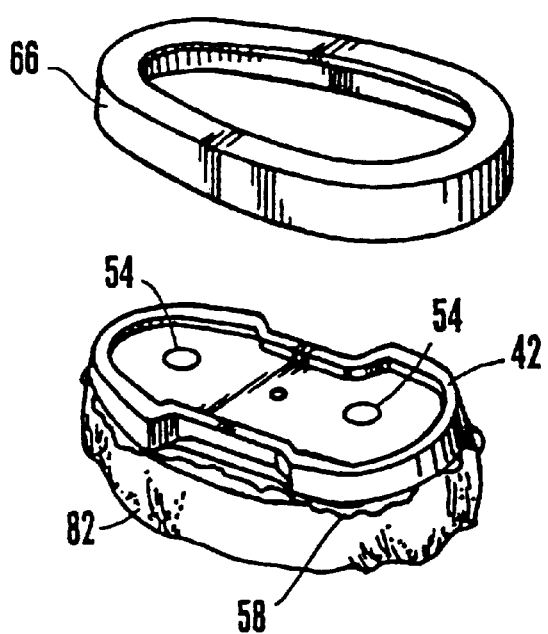
FIG. 4 is a partial perspective view showing a cement compression ring after removal from a secured tibial component in accordance with the present invention.

In FIG. 4, the impacting procedure has been completed, and the outer cement compression ring 66 is shown as having been removed from the tibial baseplate 42. Where further stabilization is desired between the baseplate 42 and the tibia 82, a pair of titanium cancellous bone screws (not shown in FIG. 4) may be received within the pair of cancellous bone screw holes 54 formed in the tibial baseplate 42.

As previously discussed, in a preferred embodiment the tibial baseplate is fabricated out of titanium. Presently, several manufacturers supply tibial baseplates that are appropriate for use with the present invention. Such manufacturers include the following: Sulzer Orthopedics, Johnson & Johnson, Biomet, and Zimmer.

The cement compression ring 66 must be shaped appropriately to receive the tibial baseplate. Preferably, the extended peripheral wall 68 is spaced no further than one (1) mm from the adjacent peripheral rim 48 of the tibial baseplate 42. A greater separation increases the likelihood of lateral bone cement leakage, as well as a reduction in the bone cement pressurization and penetration adjacent any such leakage.

The inwardly-extending seating ring is provided primarily for the convenience of the surgeon and operating room staff, and is not considered to be essential to the successful functioning of the present invention. Of greater importance is the height of the peripheral wall of the cement compression ring which should exceed the thickness of the tibial baseplate by 2–5 mm. With reference to FIG. 2, the dimension C preferably exceeds the dimension D by an amount of 2–5 mm.

The cement compression ring is preferably fabricated out of stainless steel of thickness on the order of 1 mm. Other materials, such as aluminum and hard plastic are also appropriate, with the desired thickness varying in accordance with the strength of the fabrication material used.

Our invention has been found to produce increased interdigitation of cement within the proximal tibia as compared to standard implantation techniques. It is believed that this is a result of increased cement pressure during implantation.

In one experimental evaluation [citation], eight pairs of embalmed cadaveric tibiae were harvested from donors. Each tibia was prepared for implantation of the Natural Knee II (Trademark of Sulzer Orthopedics Inc.) tibial baseplate by resecting a planar surface on the proximal end of the tibia. The right tibia of each pair was cemented using conventional cementing techniques. The backside of the tibial baseplate was completely covered with cement. The baseplate was then driven into the tibia and the excess cement was removed. In the left tibia, each baseplate was implanted using a cement compression ring that fit around the circumference of the tibial component. The ring protruded several millimeters distally from the edge of the tibial tray. Cement was then placed in the recess formed between the ring and the backside of the tibial baseplate. The assembly of baseplate, ring and cement was placed on the tibia and the baseplate was driven into the tibia. Before the baseplate reached its seated position, the compression ring came in contact with the resected surface of the tibia thereby limiting cement extrusion during the seating process.

Cement pressures at the baseplate-cement interface were measured with two electronic transducers located within the medial and lateral plateaus of the baseplate. These devices were attached to the tibial tray and were exposed to the cement mantle via medial and lateral screw holes. The pressure measurements were sampled at 100 Hz. Data collection began before the cement was placed on the distal surface of the tibial tray and continued until the cement began to set.

The pressure history of the interface during active pressurization (i.e. the time during which the component was being seated) was summarized by the following parameters: I) the duration of the pressurization, that is, seating time, II) the maximum, minimum and mean pressure recorded within the medial and lateral compartments, III) the cumulative pressure, defined by the pressure integrated with respect to time over the period of pressurization, IV) the mean positive and mean negative pressures, and V) the cumulative positive and negative pressures. Some of these measurements are reported below.

Once the cement set, the tibial components were extracted from the cement mantle. One tibia was damaged beyond repair, leaving seven pairs of tibiae available for analysis. The depth of cement penetration was measured in eight zones within the proximal tibia: Medial, Anterior-Medial, Anterior, Anterior-Lateral, Lateral, Posterior-Lateral, Posterior, and Posterior-Medial. Each Tibia was cut into eight pie-like pieces with cutting planes passing through each of the measurement zones. Approximately 100 points were measured on each of the sections to accurately approximate the bony and cement surfaces. The measured points describing the surfaces of the distal cement boundary and the proximal bony trabeculae boundary were used to calculate the distance between the most distal cement and most proximal bone surface at 1 mm increments on each of the sections. Using these measurements, the mean depth of cement penetration as well as the total area of penetration within each zone were calculated.

The results are summarized in the following tables. Table 1 records the average pressures recorded during implantation at medial and lateral locations. The average seating time, maximum, mean and cumulative pressures are given. Table 2 records the depth of penetration determined after sectioning the tibiae.

TABLE 1

Pressurization Data

| Specimen | Seating Time | Pressure [psi] | | | | Cummulative Pressure [s-psi] | |
|---|---|---|---|---|---|---|---|
| | | Max Lateral | Max Medial | Mean Medial | Mean Lateral | Medial | Lateral |
| Control | 14.72 | 34.65 | 9.23 | 1.63 | 0.85 | 19.14 | 9.92 |
| Ring | 23.78 | 42.12 | 5.51 | 2.18 | 1.91 | 48.43 | 43.07 |
| StdErr | 1.13 | 72.37 | 7.32 | 0.46 | 0.10 | 8.97 | 1.28 |
| StdErr | 2.37 | 59.08 | 3.91 | 0.18 | 0.14 | 9.68 | 4.92 |
| Change | 162% | 209% | 140% | 134% | 223% | 253% | 434% |
| P | 0.001 | 0.037 | 0.011 | 0.362 | 0.001 | 0.114 | 0.000 |

TABLE 2

Penetration Data

| Measurement Location | Mean Penetration [mm] | | | | | Mean Penetration Area [mm^2] | | | | |
|---|---|---|---|---|---|---|---|---|---|---|
| | Control | | Ring | | | Control | | Ring | | |
| | Mean | Se | Mean | se | Change | Mean | Se | Mean | se | Change |
| Med | 1.69 | 0.30 | 4.79 | 0.95 | 284% | 47.77 | 10.12 | 140.37 | 25.13 | 294% |
| Ant Med | 1.38 | 0.25 | 3.17 | 0.25 | 229% | 31.22 | 5.10 | 62.23 | 4.13 | 199% |
| Ant | 1.30 | 0.24 | 3.81 | 0.59 | 292% | 23.45 | 5.58 | 72.09 | 13.14 | 307% |
| Ant Lat | 1.27 | 0.33 | 3.36 | 0.61 | 265% | 24.06 | 6.34 | 57.09 | 12.32 | 237% |
| Lat | 1.88 | 0.37 | 3.75 | 0.63 | 199% | 49.38 | 12.34 | 99.58 | 18.29 | 202% |
| Pos Lat | 1.59 | 0.30 | 2.42 | 0.40 | 153% | 36.83 | 7.71 | 42.95 | 7.23 | 117% |
| Pos | 0.83 | 0.10 | 3.60 | 0.40 | 437% | 8.60 | 1.36 | 59.49 | 8.31 | 692% |
| Pos Med | 1.07 | 0.19 | 3.24 | 0.55 | 302% | 19.11 | 4.44 | 66.55 | 11.71 | 348% |

The data shows that there were great differences between the control tibiae and specimens prepared using the cement compression ring. One factor influencing this difference may have been that the duration of pressurization of the cement (seating time) was extended by an average of 62% by using the compression ring (14.7 sec, vs 23.8 sec) (Table 1).

Similarly, maximum cement pressures were significantly higher when the compression ring was used. In the case of the lateral compartment the difference was 209%, while in the medial compartment the difference was 140%. A significant parameter is the cumulative pressure that the cement experiences during the seating process or the time integral of pressure (P(t)dt). In these experiments, the compression ring increased the cumulative pressure by 253% in the medial compartment and 434% in the lateral compartment.

The increased maximum pressures and cumulative pressures associated with the pressurization device had a direct impact on the cement penetration depth as well as the penetration area. The average depth of cement penetration was 270% higher in the tibiae which were implanted using the pressurization device compared to the contralateral controls. The greatest difference in the depth of cement penetration, 437%, was seen in the Posterior zone, while the smallest difference, 153%, was observed in the Posterior-Lateral zone.

The total amount of cement that penetrated the trabecular structure of the tibia can be estimated from the aggregate area of cement-bone composite present on the 8 slices examined from each tibia. On average, the total area of penetration was 299% greater in the tibiae implanted with the compression ring (30.1 vs 75.0 mm$^2$). In both the control and device tibiae the greatest penetration area was observed in the Medial and Lateral zones, while the greatest difference in area was observed in the Posterior zone.

Based on this data, the cement compression ring used with a tibiae baseplate increased interdigitation of cement within the proximal tibia as compared to a standard procedure. It is expected that improved cement penetration will improve the long-term stability of an implanted prosthesis.

Our invention has been disclosed in terms of a preferred embodiment thereof, which provides for an improved tibial baseplate adhesion to the underlying bone tissue that is of great novelty and utility. Various changes, modifications, and alterations in the teachings of the present invention may be contemplated by those skilled in the art without departing from the intended spirit and scope thereof. It is intended that the present invention encompass such changes and modifications.

What is claimed is:

1. A kit for an implantable orthopedic component comprising
    an orthopedic appliance having a base plate, said base plate having a first surface adapted to abut a resected bone surface, a second surface spaced apart from said first surface, and a peripheral wall between said first surface and said second surface, and
    an articulating surface supported on said base plate, and
    a compression ring, said compression ring having an interior surface generally conforming to said peripheral wall and slidingly received thereon, said compression ring being adapted to extend beyond said first surface, forming a cavity bounded by said first surface and said compression ring.

2. The kit according to claim 1 wherein said compression ring further comprises a circumferential wall, said wall including said interior surface and an exterior surface spaced away from said interior surface and upper and lower edges connecting said interior and exterior surfaces.

3. The kit according to claim 2 wherein said compression ring further comprises a lip connected to said interior wall and extending inwardly therefrom.

4. The kit according to claim 3 wherein said lip is connected to said compression ring adjacent said upper edge.

5. The kit according to claim 3 wherein said lip is adapted to lie adjacent said second surface.

6. The kit according to claim 5 wherein said lip is connected to said compression ring adjacent said upper edge.

7. The kit of claim 1 wherein said compression ring is adapted to extend completely around said peripheral wall.

8. The kit of claim 1 wherein said compression ring is adapted to extend 2 mm to 5 mm beyond said first surface.

9. The kit according to claim 1 wherein said compression ring further comprises a lip connected to said interior wall and extending inwardly therefrom.

10. The kit according to claim 9 wherein said lip is connected to said compression ring adjacent said upper edge.

11. The kit according to claim 9 wherein said lip is adapted to lie adjacent said second surface.

12. The kit according to claim 11 wherein said lip is connected to said compression ring adjacent said upper edge.

13. A removable cement compression ring for use with an implantable orthopedic appliance, said orthopedic appliance having a first surface adapted to abut a resected bone surface, and a peripheral wall adjacent said first surface, said cement compression ring comprising an interior surface generally conforming to said peripheral wall and adapted to be slidingly received thereon, said compression ring being adapted to extend beyond said first surface, whereby a cavity may be formed, said cavity being bounded by said first surface and said compression ring.

14. The compression ring according to claim 13 further comprising a circumferential wall, said wall including said interior surface and an exterior surface spaced away from said interior surface and upper and lower edges connecting said interior and exterior surfaces.

15. The compression according to claim 14 wherein said compression ring further comprises a lip connected to said interior wall and extending inwardly therefrom.

16. The compression ring according to claim 15 wherein said lip is connected to said compression ring adjacent said upper edge.

17. The compression ring according to claim 15 wherein said lip is adapted to lie adjacent said second surface.

18. The compression ring according to claim 17 wherein said lip is connected to said compression ring adjacent said upper edge.

19. The compression ring of claim 13 wherein said compression ring is adapted to extend completely around said peripheral wall.

20. The compression ring of claim 13 wherein said compression ring is adapted to extend 2 mm to 5 mm beyond said first surface.

21. The compression ring according to claim 13 wherein said compression ring further comprises a lip connected to said interior wall and extending inwardly therefrom.

22. The compression ring according to claim 21 wherein said lip is connected to said compression ring adjacent said upper edge.

23. The compression ring according to claim 21 wherein said lip is adapted to lie adjacent said second surface.

24. The compression ring according to claim 23 wherein said lip is connected to said compression ring adjacent said upper edge.

25. A method of implanting an orthopedic component comprising
    providing an orthopedic appliance having a base plate, said base plate having a first surface adapted to abut a resected bone surface, a second surface spaced apart from said first surface, and a peripheral wall between said first surface and said second surface, and
    an articulating surface supported on said base plate,
    installing a compression ring on said appliance, said compression ring having an interior surface generally conforming to said peripheral wall and slidingly received thereon, extending said compression ring beyond said first surface, forming a cavity bounded by said first surface and said compression ring, filling said cavity with bone cement, placing said orthopedic appliance over a resected bone surface with said cavity between said appliance and said surface, and removing said compression ring.

26. The method according to claim 25 wherein the step of placing said orthopedic appliance further comprises pressing said appliance toward said resected bone surface.

27. The method according to claim 26 wherein the step of pressing said appliance further comprises contacting said resected surface with a lower edge of said compression ring and thereafter advancing said base plate slidingly within said compression ring to compress said bone cement.

28. The method according to claim 27 wherein said step of advancing said base plate comprises placing an impactor against said second surface and striking said impactor.

29. The method according to claim 28 wherein said compression ring further comprises a circumferential wall, said wall including said interior surface and an exterior surface spaced away from said interior surface and upper and lower edges connecting said interior and exterior surfaces and a lip connected to said interior wall and extending inwardly therefrom and said impactor fits within said lip.

30. The method according to claim 29 wherein said step on installing said compression ring further comprises placing said lip adjacent said second surface.

* * * * *